United States Patent
Sussman et al.

[11] Patent Number: 6,156,036
[45] Date of Patent: Dec. 5, 2000

[54] SURGICAL HANDPIECE TIP

[75] Inventors: Glenn Sussman, Lake Forest; Martin J. Padget, Huntington Beach; Donald M. Cohen, Irvine, all of Calif.

[73] Assignee: Alcon Laboratories, Inc.

[21] Appl. No.: 09/330,698

[22] Filed: Jun. 11, 1999

[51] Int. Cl.$^7$ ................................................. A61B 18/18
[52] U.S. Cl. ........................... 606/48; 606/41; 606/27; 606/49
[58] Field of Search .................. 606/27, 28, 29, 606/32, 41, 46–52; 607/96, 98, 99, 101, 104, 105, 113

[56] References Cited

U.S. PATENT DOCUMENTS

| | | |
|---|---|---|
| 3,589,363 | 6/1971 | Banko et al. . |
| 3,606,878 | 9/1971 | Kellog . |
| 3,818,913 | 6/1974 | Wallach . |
| 3,884,237 | 5/1975 | O'Malley et al. . |
| 3,913,583 | 10/1975 | Bross . |
| 3,930,505 | 1/1976 | Wallach . |
| 3,994,297 | 11/1976 | Kopf . |
| 4,024,866 | 5/1977 | Wallach . |
| 4,169,984 | 10/1979 | Parisi . |
| 4,223,676 | 9/1980 | Wuchinich . |
| 4,246,902 | 1/1981 | Martinez . |
| 4,301,802 | 11/1981 | Poler . |
| 4,326,529 | 4/1982 | Doss et al. . |
| 4,493,694 | 1/1985 | Wuchinich . |
| 4,494,539 | 1/1985 | Zenitani et al. . |
| 4,517,977 | 5/1985 | Frost . |
| 4,534,347 | 8/1985 | Taylor . |
| 4,570,632 | 2/1986 | Woods . |
| 4,577,629 | 3/1986 | Martinez . |
| 4,589,414 | 5/1986 | Yoshida et al. . |
| 4,589,415 | 5/1986 | Haaga . |
| 4,597,388 | 7/1986 | Koziol et al. . |
| 4,609,368 | 9/1986 | Dotson, Jr. . |
| 4,634,419 | 1/1987 | Kreizman et al. . |
| 4,634,420 | 1/1987 | Spinosa et al. . |
| 4,662,869 | 5/1987 | Wright . |
| 4,674,502 | 6/1987 | Imonti . |
| 4,696,298 | 9/1987 | Higgins et al. . |
| 4,706,669 | 11/1987 | Schlegel . |
| 4,753,234 | 6/1988 | Martinez . |
| 4,805,616 | 2/1989 | Pao . |
| 4,909,249 | 3/1990 | Akkas et al. . |
| 4,911,161 | 3/1990 | Schechter . |
| 4,922,902 | 5/1990 | Wuchinich et al. . |
| 4,986,827 | 1/1991 | Akkas et al. . |
| 4,989,583 | 2/1991 | Hood . |
| 4,989,588 | 2/1991 | Kubota et al. . |
| 5,009,656 | 4/1991 | Reimels . |
| 5,019,035 | 5/1991 | Missirlian et al. . |
| 5,106,364 | 4/1992 | Hayafuji et al. . |
| 5,154,694 | 10/1992 | Kelman . |
| 5,201,729 | 4/1993 | Hertzmann et al. . |
| 5,217,459 | 6/1993 | Kamerling . |
| 5,226,910 | 7/1993 | Kajiyama et al. . |

(List continued on next page.)

FOREIGN PATENT DOCUMENTS

WO 98/17190  4/1998  WIPO .

OTHER PUBLICATIONS

Cowley, Geoffrey, "Beating the Back Ache", *Newsweek*, Mar. 15, 1999.

*Primary Examiner*—Linda C. M. Dvorak
*Assistant Examiner*—R. Kearney
*Attorney, Agent, or Firm*—Jeffrey S. Schira

[57] ABSTRACT

A surgical handpiece tip with at least two coaxially spaced electrically conductive tubes. The tubes are separated by an electrical insulator. The interior of the inner tube is used for aspiration of liquefied tissue. The distal portion of the interior tube terminates just inside of the outer tube so as to form a boiling region. Electrical current is passed between the inner and outer tube to rapidly boil any surgical fluid in the boiling region. The boiling fluid rapidly expands out of the ring between the tubes and contacts the targeted tissue, thereby liquefying the tissue and allowing the tissue to be aspirated.

6 Claims, 5 Drawing Sheets

U.S. PATENT DOCUMENTS

| | | |
|---|---|---|
| 5,250,065 | 10/1993 | Clement et al. . |
| 5,261,883 | 11/1993 | Hood et al. . |
| 5,261,923 | 11/1993 | Soares . |
| 5,275,607 | 1/1994 | Lo et al. . |
| 5,277,696 | 1/1994 | Hagen ........................................ 606/49 |
| 5,284,472 | 2/1994 | Sussman et al. . |
| 5,322,504 | 6/1994 | Doherty et al. . |
| 5,423,330 | 6/1995 | Lee . |
| 5,433,739 | 7/1995 | Slujter et al. . |
| 5,562,692 | 10/1996 | Bair . |
| 5,591,184 | 1/1997 | McDonnell . |
| 5,616,120 | 4/1997 | Andrew . |
| 5,653,692 | 8/1997 | Masterson et al. . |
| 5,669,923 | 9/1997 | Gordon . |
| 5,674,226 | 10/1997 | Doherty et al. . |
| 5,865,790 | 2/1999 | Bair . |
| 5,891,095 | 4/1999 | Eggers et al. . |
| 5,925,038 | 7/1999 | Panescu et al. ........................... 606/41 |
| 6,024,733 | 2/2000 | Eggers et al. ........................... 604/500 |

…

SURGICAL HANDPIECE TIP

BACKGROUND OF THE INVENTION

This invention relates generally to the field of minimally invasive surgery, such as intervertebral disc and cataract surgery and more particularly to a handpiece for practicing the liquefraction technique.

The human eye in its simplest terms functions to provide vision by transmitting light through a clear outer portion called the cornea, and focusing the image by way of the lens onto the retina. The quality of the focused image depends on many factors including the size and shape of the eye, and the transparency of the cornea and lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. During this procedure, a thin phacoemulsification cutting tip is inserted into the diseased lens and vibrated ultrasonically. The vibrating cutting tip liquifies or emulsifies the lens so that the lens may be aspirated out of the eye. The diseased lens, once removed, is replaced by an artificial lens.

Recently, a new tissue removal technique has been developed that involves the injection of hot (approximately 45° C. to 105° C.) water or saline to liquefy or gellate tissue, such as the hard lens nucleus, thereby making it possible to aspirate the liquefied tissue. Aspiration is conducted with the injection of the heated solution and the injection of a relatively cool solution, thereby quickly cooling and removing the heated solution. One application of this technique is more fully described in U.S. Pat. No. 5,616,120 (Andrew, et al.), the entire contents of which is incorporated herein by reference. The apparatus disclosed in the publication, however, heats the solution separately from the surgical handpiece. Temperature control of the heated solution can be difficult because the fluid tubings feeding the handpiece typically are up to two meters long, and the heated solution can cool considerably as it travels down the length of the tubing.

The use of electrosurgical handpieces to remove tissue is known. For example, U.S. Pat. No. 5,009,656 (Reimels), the entire contents of which is incorporated herein by reference, describes an electrosurgical handpiece having an inner and an outer tube separated by an insulator. Current is passed between the inner and the outer tube to cause a spark that is used to cut tissue. This device intentionally creates an air gap between the electrodes to facilitate sparking, and does not use heated fluid as the cutting medium.

Therefore, a need continues to exist for a surgical handpiece that can heat internally the solution and create high pressure, high rise rate waves or pulses used to perform the liquefraction technique.

BRIEF SUMMARY OF THE INVENTION

The present invention improves upon the prior art by providing a surgical handpiece having a tip with at least two coaxially spaced electrically conductive tubes. The tubes are separated by an electrical insulator. The interior of the inner tube is used for aspiration of liquefied tissue. The distal portion of the interior tube terminates just inside of the outer tube so as to form a boiling region. Electrical current is passed between the inner and outer tube to rapidly boil any surgical fluid in the boiling region. The boiling fluid rapidly expands out of the ring between the tube ends and forces hot fluid to contact the targeted tissue, thereby liquefying the tissue and allowing the tissue to be aspirated.

Accordingly, one objective of the present invention is to provide a surgical handpiece having a tip with at least two tubes.

Another objective of the present invention is to provide a handpiece for practicing the liquefraction method of tissue removal.

Another objective of the present invention is to provide a handpiece for practicing intervertebral disc surgery.

These and other advantages and objectives of the present invention will become apparent from the detailed description and claims that follow.

DETAILED DESCRIPTION OF THE INVENTION

Figure 1:
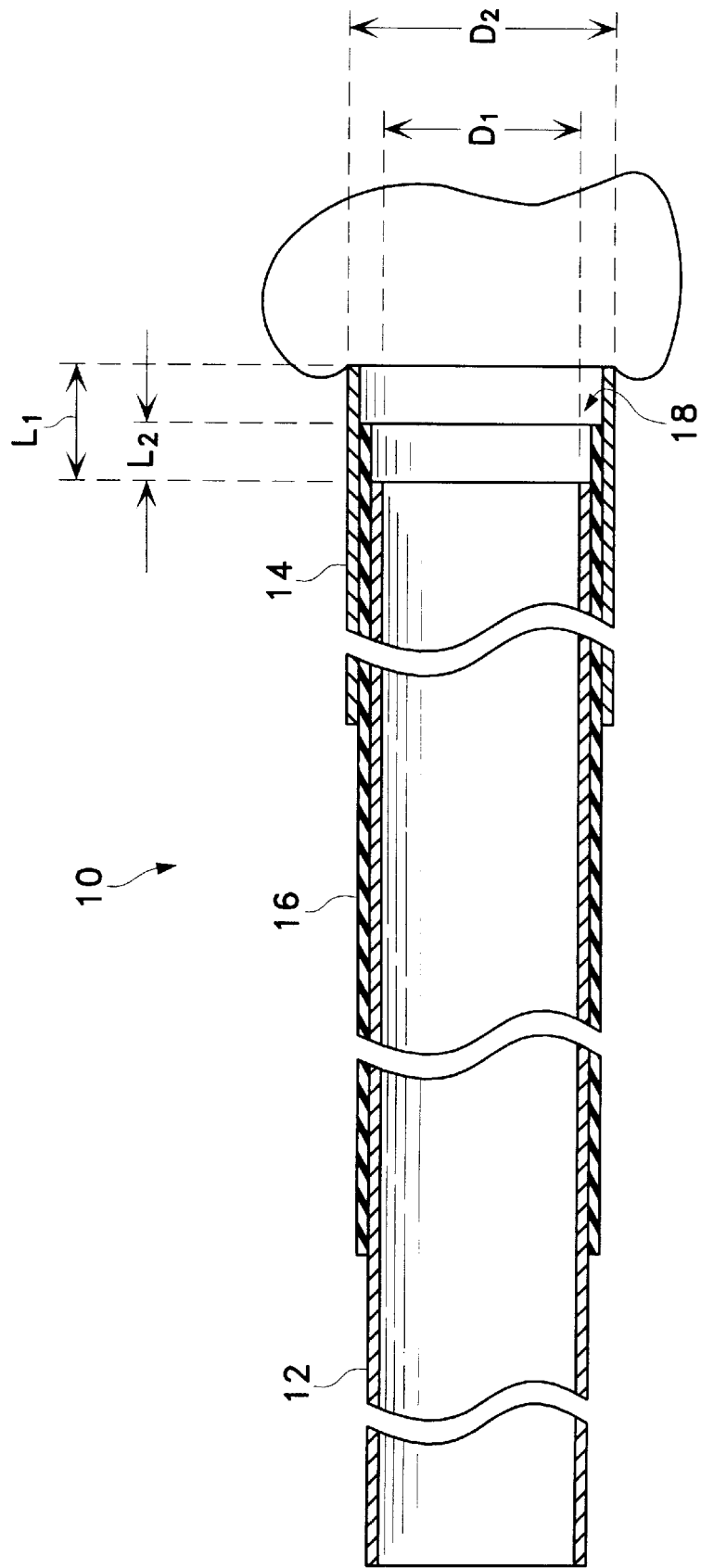
FIG. 1 is a schematic, cross-sectional view of a first embodiment of a tip that can be used with the handpiece of the present invention.
Figure 4:
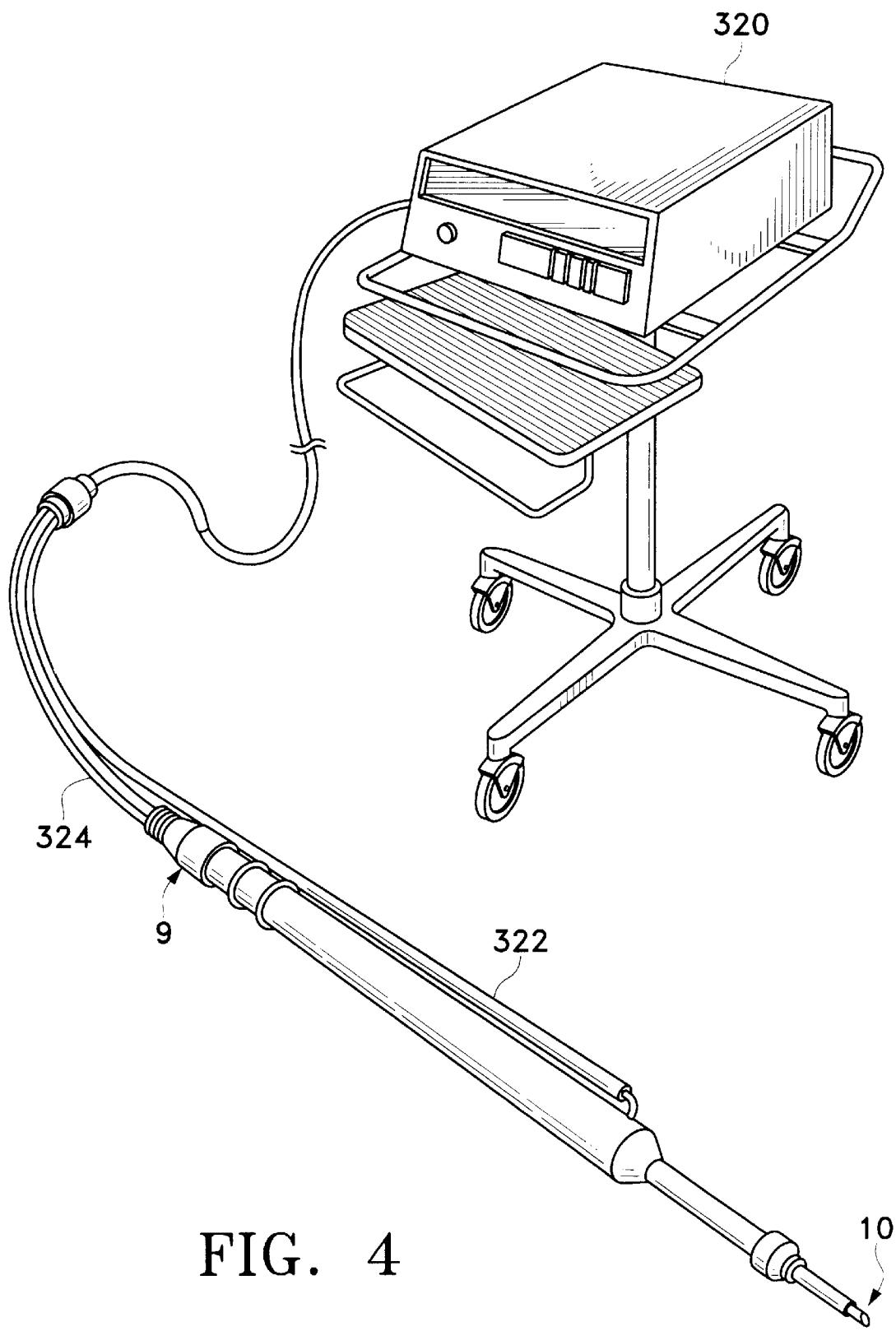
FIG. 4 is a perspective view of a handpiece and control console that may be used with the present invention.

As best seen in FIGS. 1 and 4, in the first embodiment of the present invention tip 10 to be used with handpiece 9 generally includes inner tube 12 and outer tube 14 separated by insulator 16. Inner tube 12 has an inside diameter $D_1$ of between 0.010 inches and 0.050 inches, with 0.030 being preferred, and an outside diameter of between 0.015 inches and 0.060 inches, with 0.036 inches being preferred. Outer tube 14 has an outside diameter $D_2$ of between 0.025 inches and 0.075 inches, with 0.045 inches being preferred. Inner tube 12 and outer tube 14 may be made of any electrically conductive material, such as stainless steel or titanium tubing. Insulator 16 may be made of any electrically non-conductive material resistant to high temperatures, such as polyimide, silicone or ceramic. Insulator 16 may be any suitable thickness, but between 0.001 inches and 0.003 inches is preferred, with 0.002 inches being most preferred.

Outer tube 14 extends distally past inner tube 12 a distance $L_1$ of between 0.010 inches and 0.030 inches, with 0.020 inches being preferred. Insulator 16 may be flush with inner tube 12 or may extend distally past inner tube 12 a distance $L_2$ of between 0.00 inches and 0.020 inches. The space between outer tube 14 and inner tube 12 forms boiling region 18. While only two embodiments of the tip of the present invention are disclosed herein, any tip producing adequate pressure pulse force, rise time and frequency may also be used. For example, any suitable tip producing a pressure pulse force of between 0.03 grams and 20.0 grams, with a rise time of between 1 gram/sec and 20,000 grams/ sec, with between 3000 grams/sec and 20,000 grams/sec being more preferred and a frequency of between 1 Hz and 400 Hz may be used, with between 25 Hz and 200 Hz being most preferred.

In use, surgical fluid (e.g. saline irrigating solution) enters boiling region 18. Electrical current (preferably Radio Frequency Alternating Current "RFAC") is delivered to and across inner tube 12 and outer tube 14 through the surgical fluid in boiling region 18 because of the conductive nature of the surgical fluid. As the current flows through boiling region 18, the surgical fluid boils. As the surgical fluid boils, it expands rapidly out of tip 10. Subsequent pulses of electrical current form sequential gas bubbles. The size and pressure of the fluid pulse obtained by boiling region 18 can be varied by varying the length, timing and/or power of the electrical pulse sent to tubes 12 and 14 and by varying the dimensions of boiling region 18.

Figure 2:
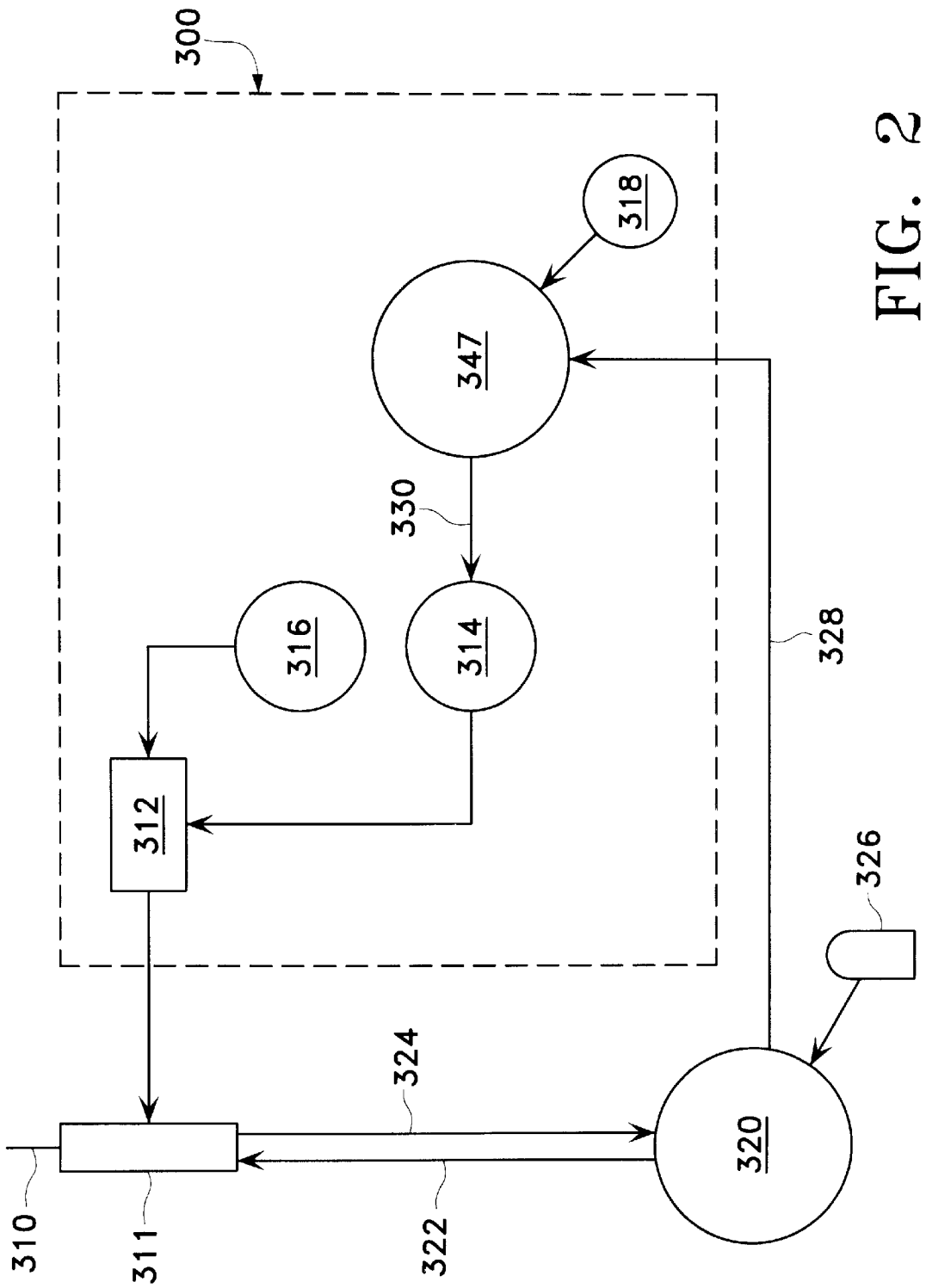
FIG. 2 is a block diagram of a first control system that can be used with the surgical handpiece of the present invention.
Figure 5:
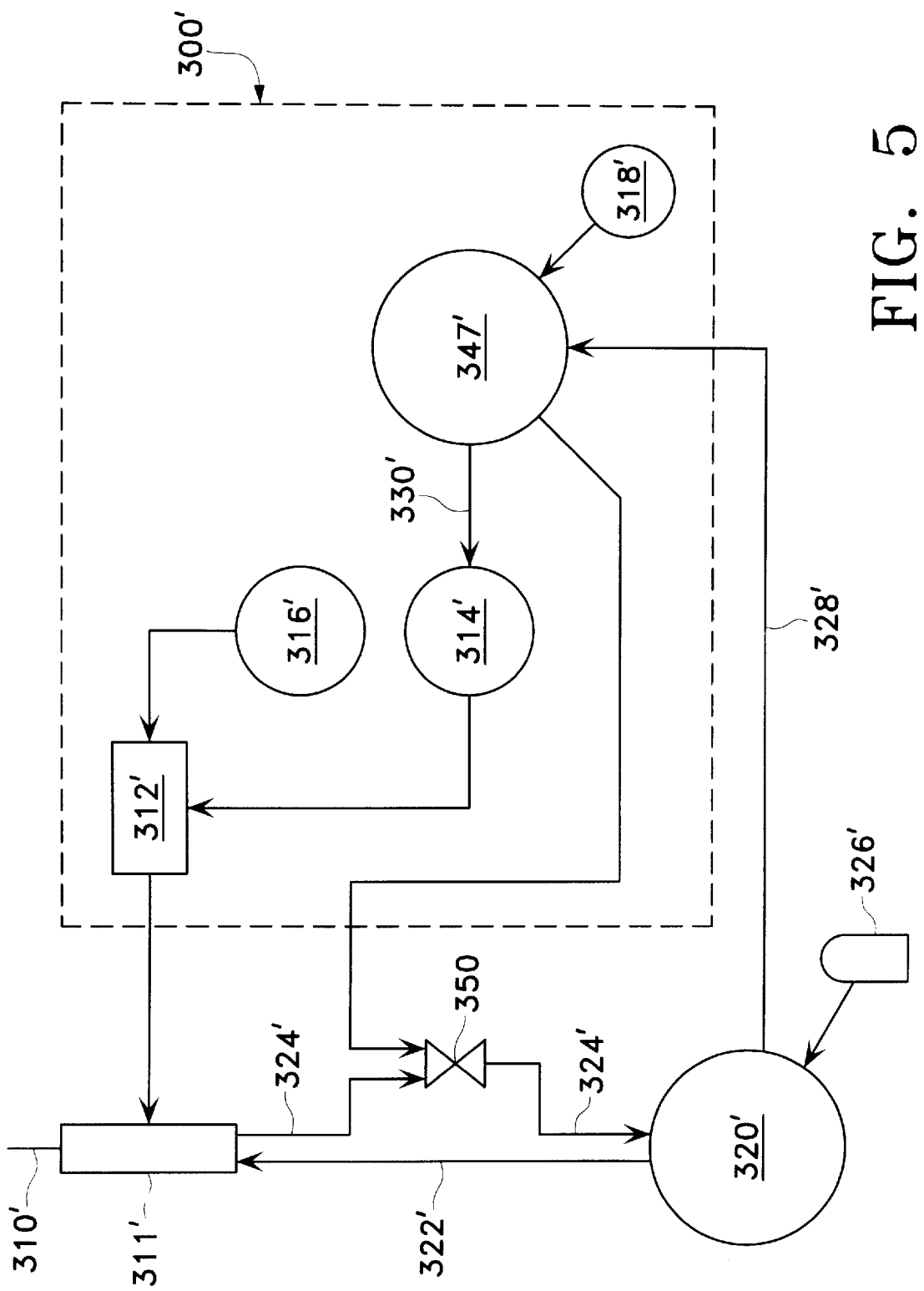
FIG. 5 is a block diagram of a second control system that can be used with the surgical handpiece of the present invention which is similar to the control system illustrated in FIG. 2 except for the addition of a control valve in the aspiration line.

As seen in FIGS. 2, 4 and 5, control system 300 or 300' for use in operating handpiece 9, 311 or 311' containing tip 10, 110, 310 or 310' includes control module 347 or 347', RF amplifier 312 or 312' and function generator 314 or 314'. Power is supplied to RF amplifier 312 or 312' by DC power supply 316 or 316', which preferably is an isolated DC power supply operating at ±200 volts. Control module 347 or 347' may be any suitable microprocessor, and may receive input from operator input device 318 or 318'. Function generator 314 or 314' provides the electric wave form to amplifier 312 or 312' and preferably operates at 200 KHz to 10 MHz, and more preferably between 450 KHz and 1 MHZ, to help minimize corrosion.

In use, control module 347 or 347' receives input from surgical console 320 or 320'. Console 320 or 320' may be any commercially available surgical control console such as the LEGACY® SERIES TWENTY THOUSAND® surgical system available from Alcon Laboratories, Inc., Fort Worth, Tex. Console 320 or 320' is connected to handpiece 9, 311 or 311' through irrigation line 322 or 322' and aspiration line 324 or 324', and the flow through lines 322 or 322' and 324 or 324' is controlled by the user via footswitch 326 or 326'. Irrigation and aspiration flow rate information in handpiece 9, 311 or 311' is provided to control module 347 or 347' by console 320 or 320' via interface 328 or 328', which may be connected to the ultrasound handpiece control port on console 320 or 320' or to any other output port. Control module 347 or 347' uses footswitch 326 or 326' information provided by console 320 or 320' and operator input from input device 318 or 318' to generate two control signals 330 or 330' and 332 or 332'. Signal 330 or 330' is used to control function generator 314 or 314'. Based on signal 330 or 330', function generator 314 or 314' provides a wave form at the operator selected frequency and amplitude determined by the position of footswitch 326 or 326' to RF amplifier 312 or 312' which is amplified to advance the powered wave form to tip 10, 110, 310 or 310' to create heated, pressurized pulses of surgical fluid.

As best seen in FIG. 5, control system 300' may also use valve 350 placed in aspiration line 324'. Valve 350 is controlled by control module 347' to alternate between an open and a closed position, thereby creating pulsed aspiration flow.

Figure 3:
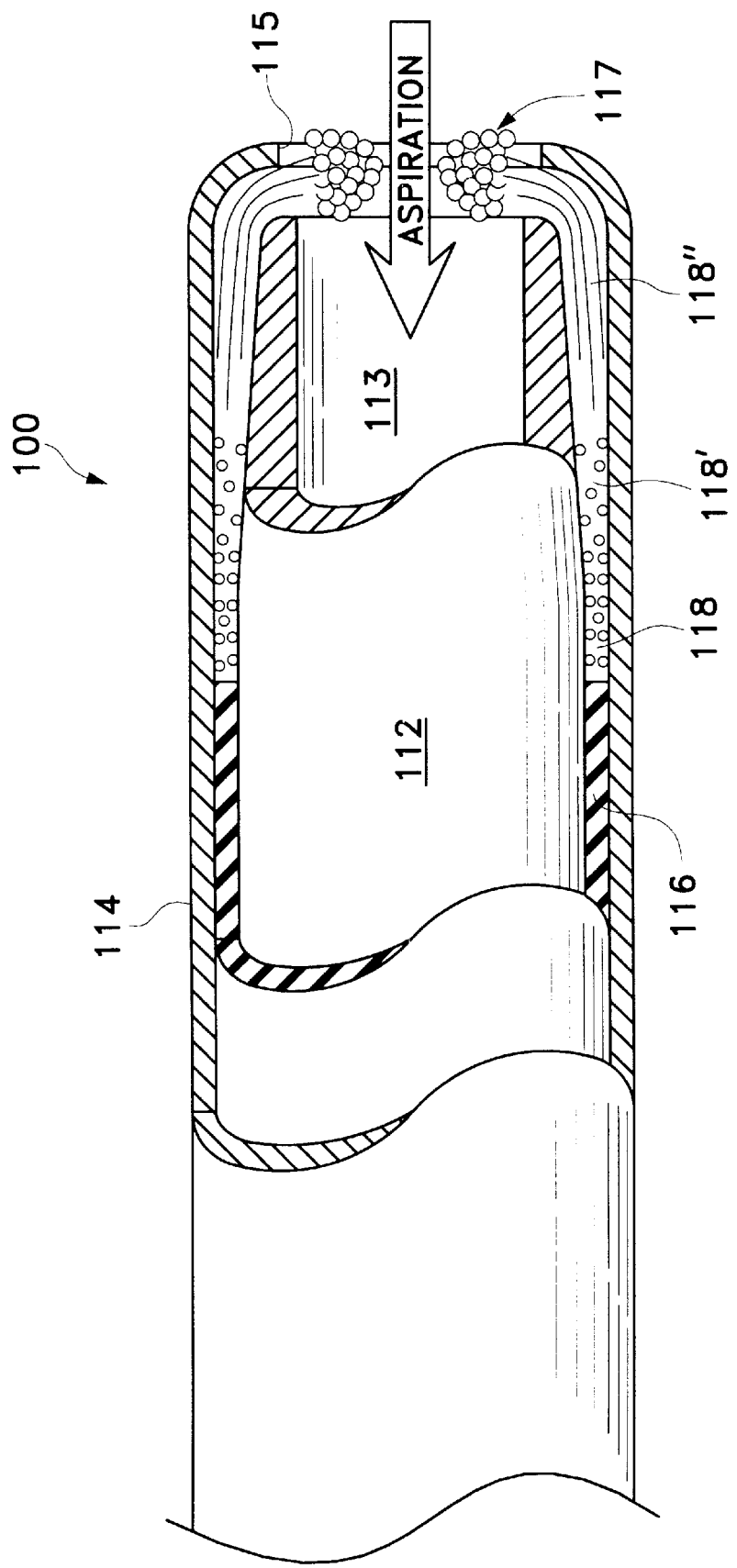
FIG. 3 is a schematic, cross-sectional view of a second embodiment a tip that can be used with the handpiece of the present invention.

As best seen in FIG. 3, in a second embodiment of the present invention, tip 110 which may be used with handpiece 9 or 311 generally includes inner tube 112 and outer tube 114 separated by insulator 116. Inner tube 112 has a generally conical distal end 113. Conical end 113 creates a boiling region 118 between inner tube 112 and outer tube 114 that generally increases in size from region 118 to region 118' and 118". As current flows between outer tube 114 and inner tube 112, boiling begins at region 118 where the electrode gap is the smallest. As the fluid in area 118 boils, the resistance to current flow is increased as the fluid turns to steam or vapor. In this manner, the boiling of the fluid moves sequentially from region 118 to region 118' and then to region 118" where the steam escapes out port 115 in outer tube 114 where the steam and/or heated fluid liquefies the targeted tissue at region 117 adjacent to port 115.

The present invention may also be used for intervertebral disc surgery, such as intradisc thermal annuloplasty. During this surgery, the ligaments encasing a spinal disc are heated to destroy invading veins and nerves and to shrink the ligaments to seal any tears or ruptures. This surgical procedure is more completely described in U.S. Pat. Nos. 5,201,729 and 5,433,739 and in U.S. patent application Ser. Nos. 08/881,525, 08/881,527, 08/881,692, 08/881,693 and 08/881,694 which correspond to WIPO Publication No. WO 98/17190, the entire contents of which are incorporated herein by reference.

This description is given for purposes of illustration and explanation. It will be apparent to those skilled in the relevant art that changes and modifications may be made to the invention described above without departing from its scope or spirit. For example, it will be recognized by those skilled in the art that the present invention may be combined with ultrasonic and/or rotating cutting tips to enhance performance.

We claim:

1. A handpiece tip comprising:
    a) an inner electrically conductive aspiration tube having a distal end;
    b) an outer electrically conductive tube having a distal end coaxially spaced about the inner tube, the distal end of the outer tube extending distally past the distal end of the inner tube;
    c) an insulator spaced between the inner tube and the outer tube; and
    b) a boiling region formed by the outer tube between the distal end of the outer tube and the distal end of the inner tube.

2. The tip of claim 1 wherein the electrical current flowing across the inner and outer electrically conductive tubes is capable of boiling a fluid.

3. The tip of claim 1 wherein the inner tube has a conical distal end.

4. The tip of claim 1 wherein the electrical current flowing across the inner and outer electrically conductive tubes is capable of producing a pressure pulse force of between 0.03 grams and 20.0 grams in a fluid.

5. A handpiece tip comprising:
    a) an inner electrically conductive aspiration tube having a conical distal end;
    b) an outer electrically conductive tube having a distal end coaxially spaced about the inner tube, the distal end of the outer tube extending distally past the distal end of the inner tube;

c) an insulator spaced between the inner tube and the outer tube; and d) a boiling region formed by the outer tube between the distal end of the outer tube and the distal end of the inner tube, the boiling region capable of producing a pressure pulse force of between 0.03 grams and 20.0 grams in a fluid.

6. A method of performing intervertebral disc surgery, comprising the steps of:

a) inserting a handpiece tip into a selected region of an intervertebral disc, the tip having
   i. an inner electrically conductive aspiration tube having a distal end,
   ii. an outer electrically conductive tube having a distal end coaxially spaced about the inner tube, the distal end of the outer tube extending distally past the distal end of the inner tube,
   iii. an insulator spaced between the inner tube and the outer tube and
   iv. a boiling region formed by the outer tube between the distal end of the outer tube and the distal end of the inner tube;

b) applying electrical current between the inner aspiration tube and the outer tube so as to cause a fluid in the boiling chamber to boil; and c) directing the boiling fluid to the selected region of the intervertebral disc.

\* \* \* \* \*